United States Patent [19]
Greenberg

[11] Patent Number: 4,587,265

[45] Date of Patent: May 6, 1986

[54] **INHIBITION OF DIARRHEA INDUCED BY *ESCHERICHIA COLI* HEAT-STABLE ENTEROTOXIN**

[75] Inventor: Richard N. Greenberg, Kirkwood, Mo.

[73] Assignee: St. Louis University, St. Louis, Mo.

[21] Appl. No.: 464,702

[22] Filed: Feb. 7, 1983

[51] Int. Cl.$^4$ ............................................. A61K 31/195
[52] U.S. Cl. ..................................... 514/562; 514/867
[58] Field of Search ......................... 424/319; 514/562

[56] References Cited

PUBLICATIONS

CAs 66:12694e, 1966.
CAs 84:12,371u, 1976.
CAs 85:87,231c, 1976.
Broughler et al., J. Biol. Chem 254:12450–12454, 1979.
Mittal et al., PNAS, 74:4360–4364 1977.

*Primary Examiner*—Jerome D. Goldberg
*Assistant Examiner*—Jr. Rollins
*Attorney, Agent, or Firm*—Senniger, Powers, Leavitt and Roedel

[57] ABSTRACT

Substantially nontoxic materials such as cysteamine constituting a source of sulfhydryl groups are useful in inhibiting diarrhea induced by *Escherichia coli* heat-stable enterotoxin. Such materials block ST-induced secretion prior to the formation of cyclic GMP without interference with normal basal activity or metabolism and may inactivate ST itself by breaking disulfide bridges.

5 Claims, 2 Drawing Figures

INHIBITION OF DIARRHEA INDUCED BY ESCHERICHIA COLI HEAT-STABLE ENTEROTOXIN

BACKGROUND OF THE INVENTION

This invention relates to methods of inhibiting diarrhea induced by *Escherichia coli* heat-stable enterotoxin and, more particularly, to such methods which involve the use of substantially nontoxic materials providing a source of sulfhydryl groups.

As is known, entertoxigenic *Escherichia coli* may produce a heat-labile toxin or a heat-stable toxin (ST). Both are important causes of diarrheal disease in humans and domestic animals. ST specifically activates the particulate fraction of guanylate cyclase in intestinal mucosal cells (Hughes et al., *Clin. Res.* 26:524A, 1978), resulting in increased mucosal cell cyclic guanosine monophosphate (GMP) levels and a net increase in intestinal fluid secretion (Hughes et al., *Nature* (London) 271: 755–756, 1978).

Although the precise regulation of guanylate cyclase activity and cyclic GMP accumulation in vivo are unknown, several studies suggest that free radicals activate guanylate cyclase and that guanylate cyclase activity is influenced by the oxidation-reduction state of the cell and by intracellular levels of thiols and disulfides (Brandwein et al., *J. Biol. Chem.*, 256:2958–2962, 1981; Broughler et al., *J. Biol. Chem.*, 254:12450–12454, 1979; Craven et al., *Cancer Res.*, 37:4088–4097, 1977; Katsuki et al., *J. Cyclic Nucleotide Res.*, 3:23–35, 1977; Mittal et al., *Proc. Natl. Acad. Sci. U.S.A.*, 74:4360–4364, 1977; Murad et al., *Adv. Cyclic Nucleotide Res.*, 11:175–204, 1979; and White et al., *J. Biol. Chem.*, 251:7304–7312, 1976). Butylated hydroxyanisole, a free radical scavenger, significantly reduces both ST activation of guanylate cyclase and ST-induced intestinal fluid secretion (Guerrant et al., *J. Infect. Dis.*, 142:220–228, 1980). Also, hydroxylamine, an agent that activates guanylate cyclase by the production of free radicals (Kimura et al., *J. Biol. Chem.*, 250:8016–8022, 1975), causes intestinal ion transport alterations similar to those seen with ST (Field, *Rev. Infect. Dis.*, 1:918–925, 1979). Recently, Brandwein et al., supra, demonstrated that the disulfide compound cystamine could almost completely inactivate a highly purified preparation of guanylate cyclase. These findings may relate to the mechanism of action of ST or, alternatively, that thiols or disulfides might alter binding of ST to its receptor or alter subsequent ST activation of particulate guanylate cyclase. Staples et al. (*J. Biol. Chem.*, 255:4716–4721, 1980) have reported that their ST preparation lost activity on treatment with reducing agents.

There remains a need for a practical means for inhibiting diarrhea induced by *Escherichia coli* heat-stable enterotoxin.

SUMMARY OF THE INVENTION

Among the several objects of the invention may be noted the provision of a method for inhibiting or controlling diarrhea induced by *Escherichia coli* heat-stable enterotoxin; and the provision of such a method which blocks ST-induced secretion prior to the formation of cyclic GMP without interference with normal basal activity or metabolism. Other objects will be in part apparent and in part pointed out hereinafter.

Briefly, the present invention is directed to a method of inhibiting diarrhea induced by *Escherichia coli* heat-stable enterotoxin comprising the administration to mammals afflicted with such diarrhea of a material, such as cysteamine, cysteine and the like, constituting a source of sulfhydryl groups in an amount sufficient to inhibit such diarrhea.

DESCRIPTION OF THE PREFERRED EMBODIMENTS

Figure 1:
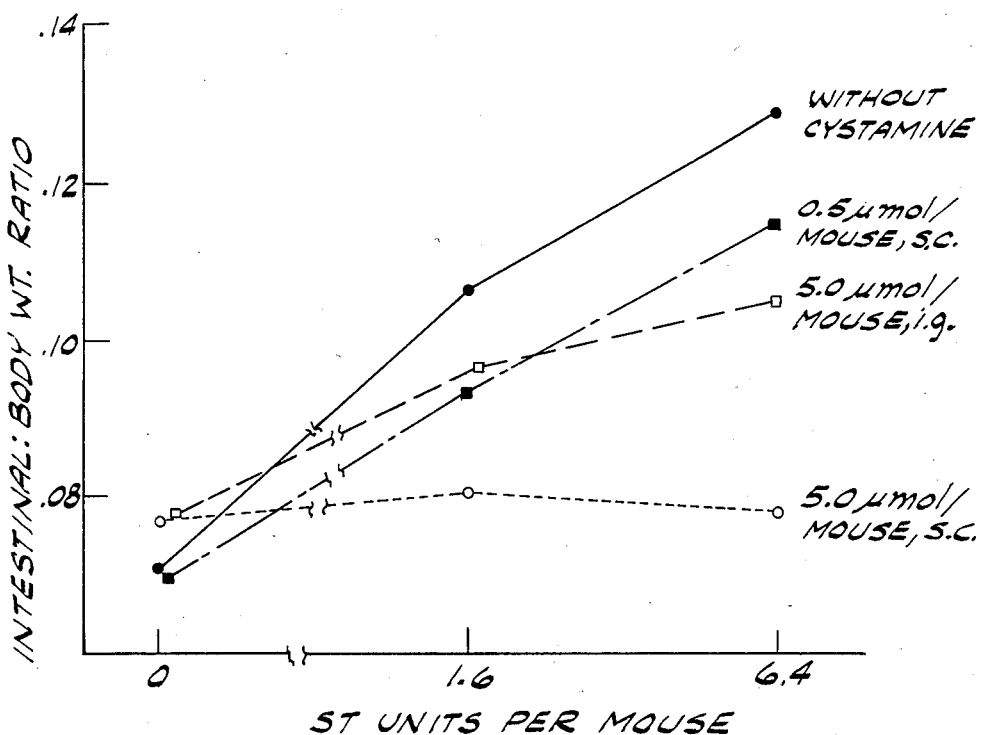
FIG. 1 is a graph depicting the results obtained in studies as to the effect of cystamine on the inhibition of ST-induced fluid secretion in suckling mice.

In accordance with the present invention, it has now been found that substantially nontoxic materials constituting a source of sulfhydryl (—SH) groups are effective for the purpose of inhibiting diarrhea induced by *Escherichia coli* heat-stable enterotoxin. Advantageously, as shown by the experimental studies set forth hereinafter, such materials which provide a source of sulfhydryl groups inhibit ST-mediated fluid secretion prior to ST-induced formation of cyclic GMP and do not interfere with normal basal activity or with normal cell function in regard to guanylate cyclase. It is believed that such materials, for example cysteamine, may directly alter the toxin without a nonspecific inhibitory effect on basal guanylate cyclase activity. Also, such materials are relatively nontoxic and therefore suitable for administration to mammals including man and domestic animals.

Among the materials constituting a source of sulfhydryl groups, which may be used in the practice of the invention, may be mentioned sulfhydryl or thiol compounds such as cysteamine, cysteine, acetylcysteine, methanethiol (methyl mercaptan), ethanethiol, 1-propanethiol, 2-propanethiol, thioacetic acid, n-butyl-4-mercaptopropionate, n-butylthioglycolate, ethyl thioglycolate, methyl thioglycolate, 3-mercaptopropionic acid, thioglycolic acid, thiolactic acid (2-mercaptopropionic acid) and thiomalic acid. Other thiol, thio or mercapto compounds or materials of this type may also be employed as the source of sulfhydryl groups. These materials may be substituted or unsubstituted and include, for example, compounds such as S-2-(3-aminopropylamino)ethyl phosphorothionic acid and S(2-aminoethyl)phosphorothioic acid which provide a source of sulfhydryl groups and have been employed heretofore as radioprotective agents (Apffel et al., *Cancer Research*, 35:429–437, 1975).

In addition, the present invention may be carried out using as the source of sulfhydryl groups a suitable substrate for binding the sulfhydryl groups and which permits these groups to be exposed and available for the purposes of the present invention. Such a suitable substrate is an agarose type gel marketed under the trade designation "Affi-Gel 401" by Bio-Rad, Richmond, Calif., which contains sulfhydryl terminal groups. This material is supplied for use in 0.01 M Tris buffer, pH 7.5 with 0.02% sodium azide as preservative and with 0.01 M dithiothreitol as antioxidant. Other such substrates including various agarose type gels, gels or beads marketed under the trade designation "Sephadex" (Pharmacia, Piscataway, N.J.) and like materials may also be utilized as the source of sulfhydryl groups.

The results of the studies set forth hereinafter show the effects of thiol and disulfide compounds on the activity of ST. As mentioned, Staples et al., supra, have reported that their purified ST loses biological activity promptly on exposure to the reducing agents 2-mercaptoethanol and dithiothreitol, and have suggested that the activity of ST depends upon the presence of disulfide bridges. The particular ST used by Staples et al., produced by an *E. coli* isolated from an infant with diarrhea, contains 6 half-cystine amino acids suggesting the presence of multiple disulfide bridges. Most other purified preparations of ST, isolated from animal strains of *E. coli*, have confirmed the presence of multiple residues of half-cystine (Alderete et al., *Infect. Immun.*, 19:1021–1030, 1978; Frantz et al., *Infect. Immun.*, 33:193–198, 1981; and Kapitany et al., *Infect. Immun.*, 24:965–966. 1979).

The enterotoxin effects of ST have been recently reviewed and many investigators have noted that ST causes an increase in intestinal cell cyclic GMP concentrations (Greenberg et al., *Pharmac. Ther.*, 13:507–531, 1981). It has also been shown that disulfide compounds, such as cystamine, and thiol compounds have very marked effects on guanylate cyclase activity (Broughler et al., supra, and Mittal et al., supra). Investigators have speculated that these agents alter the oxidation-reduction state of cellular components and thus alter guanylate cyclase activity. In addition, Brandwein et al., supra, have shown that when $^{35}$S-cystine and purified soluble guanylate cyclase are incubated together the radioactivity is incorporated into the enzyme and there is a reversible loss of enzyme activity.

The studies reported hereinafter examined the effects of various disulfide and thiol compounds on ST-induced intestinal secretion in suckling mice, ST-activation of guanylate cyclase and cyclic GMP-induced intestinal secretion in suckling mice. The results show that the disulfide compound cystamine at 1 mM reduced by 45% basal particulate guanylate cyclase activity in a rat intestinal mucosal cell preparation. Cystamine at 1 mM inhibited ST activation of the guanylate cyclase preparation by 73%. Cystamine at 5 μmol per mouse given either i.g. or s.c. could also reduce ST-induced intestinal secretion in suckling mice. Cystamine was most effective when given s.c. and, at 5 μmol per mouse, could significantly reduce secretion in mice resulting from a high ST dose (6.4 ST units). Cystamine had no effect on 8-bromo cyclic GMP-induced intestinal secretion. The results thus demonstrate that the disulfide compound altered basal and stimulated guanylate cyclase activity. The fact that cystamine inhibited ST-activated guanylate cyclase significantly more than basal activity indicates that cystamine limits maximal guanylate cyclase activity or that it may have an additional effect on ST or on ST binding. The inhibition of ST-induced secretion by cystamine clearly occurs before the formation of cyclic GMP, as cystamine has no inhibiting effect on 8-bromo cyclic GMP-induced intestinal fluid secretion.

Two other disulfide compounds, D and L-cystine were not as effective as cystamine. Neither compound inhibited basal guanylate cyclase activity. Both, however, at 1 mM, significantly reduced ST-induced guanylate cyclase activity and intestinal secretion by a low dose of toxin. The inhibition could be overcome by a higher dose of ST. Neither compound altered cyclic GMP-induced intestinal secretion. Both of these disulfide compounds appeared to alter ST-induced secretion before cyclic GMP formation. Both the D and L-isomers performed in the same manner.

The sulfhydryl compounds, i.e, cysteamine, acetylcysteine and D- and L-cysteine, at 1 mM concentration, did not alter basal guanylate cyclase activity; each, however, reduced ST-stimulated guanylate cyclase activity by 11% to 21%. In the suckling mouse, cysteamine was the most effective agent as it significantly reduced a 1.6 ST unit induced secretion with as little as 0.05 μmol per mouse, administered by intragastric (i.g.) injection. Cysteamine was less effective when given subcutaneously (s.c.). None of these sulfhydryl compounds altered 8-bromo cyclic GMP-induced intestinal secretion. These agents thus appear to be more specific inhibitors of ST than cystamine as none showed significant alteration of basal guanylate cyclase activity. In common with the disulfide agents, the compounds containing sulfhydryl groups inhibit ST effects prior to the formation of cyclic GMP.

Cystathionine, a sulfur-containing compound without a sulfhydryl or disulfide group, showed no alteration of basal or ST- or cyclic GMP-induced responses.

In summary, cysteamine and other sulfhydryl compounds inhibit ST-mediated fluid secretion prior to ST-induced formation of cyclic GMP. Cysteamine appeared to be the most effective inhibitory agent and may directly alter the toxin without a nonspecific inhibitory effect on basal guanylate or cyclase activity. On the other hand, and in contrast, disulfide compounds such as cystamine and cystine inhibited the secretory and guanylate cyclase responses to ST, perhaps by altering the cyclase enzyme directly.

The following illustrates the practice of the invention.

In this study, tissue preparation for guanylate cyclase assay was prepared from Sprague-Dawley rats (weighing 200–300 g each). Rats were sacrificed by decapitation. The lower half of the small bowel was removed and rinsed with ice cold saline. The small intestinal tract was everted to allow scraping of the mucosa. Mucosa was homogenized at 4° C. in 0.25 M sucrose containing 50 mM Tris-HCl (pH 7.9), 1 mM EDTA and 1 mM dithiothreitol. Homogenates were centrifuged at 105,000× g at 4° C. for 1 hour. Particulate fractions were stored at −60° C. and used within 1 month.

Guanylate cyclase activity was determined by guanylate cyclase assay as described in Greenberg et al., ("Inhibition of *Escherichia coli* Heat-Stable Enterotoxin Effects on Intestinal Guanylate Cyclase and Fluid Secretion by Quinacrine," *Biochem. Pharmac.* 31:2005–2009 (1982)). Cyclic GMP formed was determined by radioimmunoassay with acetylation of samples (Brandwein et al., "Reversible Inactivation of Guanylate Cyclase by Mixed Disulfide Formation," *J. Biol. Chem.*, 256:2958–2962 (1981) and Harper et al., "Femtomole Sensitive Radioimmunoassay for Cyclic AMP and Cyclic GMP after 2'0 Acetylation by Acetic Anhydride in Aqueous Solution," *J. Cyclic Nucleotide Res.*, 1:207–218 (1975). Protein was solubilized in 1 N NaOH and quantitated by the method of Lowry et al. ("Protein Measurement with the Folin Phenol Reagent," *J. Biol. Chem.*, 193:265–275 (1951)), using bovine serum albumin as standard.

The suckling mouse assay was performed as described in Greenberg et al. ("Inhibition of *Escherichia coli* Heat-Stable Enterotoxin by Indomethacin and Chlorpromazine," *Infect. Immun.*, 29:908–913 (1980)). Test solutions were either prepared in 50 mM Tris-HCl (pH 7.6) or water. The pH of all test solutions before the addition of ST was between 7 to 8. The ratio of intestinal weight to remaining body weight was determined after 3 hours (Dean et al., "Test for *Escherichia coli* Enterotoxin Using Infant Mice: Application in a Study of Diarrhea in Children in Honolulu," *J. Infect. Dis.*, 125:407-411 (1972) and Giannella, "Suckling Mouse Model for Detection of Heat-Stable *Escherichia coli* Enterotoxin: Characteristics of the Model, *Infect. Immun.*, 14:95-99 (1976)). In some instances, 0.05 ml of test agent was given subcutaneously (s.c.) prior to or at the time of an intragastric (i.g.) injection of ST or 8-bromo cyclic GMP. The osmolality of the i.g. solutions given to the mice ranged from 15 to 202 milliosmoles per liter. Solutions made in water ranged in osmolality from 15 to 50 milliosmoles per liter (water only or with maximum test amount of agents in water, respectively). Solutions made in Tris-HCl buffer ranged in osmolality from 63 to 202 milliosmoles per liter (Tris only or with maximum test amount of agents in buffer, respectively).

A semipurified ST preparation was prepared as described in Greenberg et al. ("Lanthanum Chloride Inhibition of the Secretory Response to *Escherichia coli* Heat-Stable Enterotoxin," *Infect. Immun.*, 35:483-488 (1982)). A more purified ST, made from the same material, was used in the guanylate cyclase assays. Following the protocol of Alderete and Robertson ("Purification and Chemical Characterization of the Heat-Stable Enterotoxin Produced by Porcine Strains of Enterotoxigenic *Escherichia coli*," *Infect. Immun.*, 19:1021-1030 (1978)), the material was subjected to acetone fractionation and preparative gel electrophoresis. The preparation was then further purified by gel filtration chromatography using a Bio-Gel P-6 column. The resulting effective dose of the preparation was 100 ng protein.

The reagent-grade cystamine, cysteamine, D- and L-cystine, D- and L-cysteine, cystathionine, 8-bromo cyclic GMP, sucrose, EDTA, and dithiothreitol were obtained from Sigma Chemical Co. Acetylcysteine was obtained from Mead-Johnson and Co. Other reagents were obtained as described by Hughes et al. ("Role of Cyclic GMP in the Action of Heat-Stable Enterotoxin *Escherichia coli*," *Nature* (London) 271:755-756 (1978)).

The standard error of the mean was calculated by pooling data from all experiments. The two-tailed Student's t-test was used to test the significance of the differences between the mean values.

Results

Inhibition of ST activation of guanylate cyclase.

Table 1 summarizes the effects of the various sulfhydryl and disulfide compounds on basal and ST activated (6 ST units/ml) intestinal guanylate cyclase activity. This concentration of ST results in a 2.5 fold increase of guanylate cyclase activity. Cystamine, 1 mM, inhibited ST activation of guanylate cyclase by 73%, while inhibiting basal activity by 45%. The inhibition of ST induced guanylate cyclase activity increased to 82% at 10 mM cystamine, with a 54% inhibition of basal activity. At the lower concentration of 0.1 mM, ST-induced guanylate cyclase activity was reduced by 32%, with a reduction in basal activity of only 13%.

Two other disulfide compounds, L-cystine and D-cystine were also tested. Because of precipitation of these reagents, concentrations greater than 1 mM could not be studied. At 1 mM neither drug affected basal activity but both L-cystine and D-cystine inhibited ST-induced activity of guanylate cyclase, 39% and 33% respectively.

Among the thiol compounds, cysteamine (1 mM) inhibited ST-induced guanylate cyclase activity by 21%. At this concentration cysteamine did not affect basal activity. At a higher concentration, 10 mM, cysteamine inhibited basal activity by 15%, and reduced ST-induced activity by 63%. None of the other sulfhydryl compounds (1 mM) affected basal enzyme activity but each reduced ST-activated enzyme activity: acetylcysteine—15%, L-cysteine—11%, D-cysteine—16%. At 10 mM, these compounds only slightly altered basal activity (0 to 14%), but inhibited ST-activated enzyme by 38% to 57%.

Cystathionine, a compound consisting of serine and homocysteine linked by a sulfur molecule, had no effect on either basal or ST-activated enzyme activity. Cystathionine was examined because of its structural resemblance to the disulfides and sulfhydryl agents, with the important differences of not having its sulfur as a disulfide or thiol.

TABLE 1

Percent inhibition of basal and ST-activated guanylate cyclase activity by selected disulfide and thiol compounds

| | Concentration mM) | % Inhibition | |
|---|---|---|---|
| | | Basal | ST-activated (6 units/ml) |
| Cystamine | 1.0 | 45% | 73% |
| L-cystine | 1.0 | 0% | 39% |
| D-cystine | 1.0 | 0% | 33% |
| Cysteamine | 1.0 | 0% | 21% |
| Acetylcysteine | 1.0 | 0% | 14% |
| L-cysteine | 1.0 | 0% | 11% |
| D-cysteine | 1.0 | 0% | 16% |

Inhibition of ST-induced fluid secretion in suckling mice

Significant inhibition of ST induced fluid secretion was found by all sulfhydryl and disulfide compounds but not by cystathionine. Each agent was examined both by s.c. administration and by i.g. administration.

Cystamine

Figure 2:
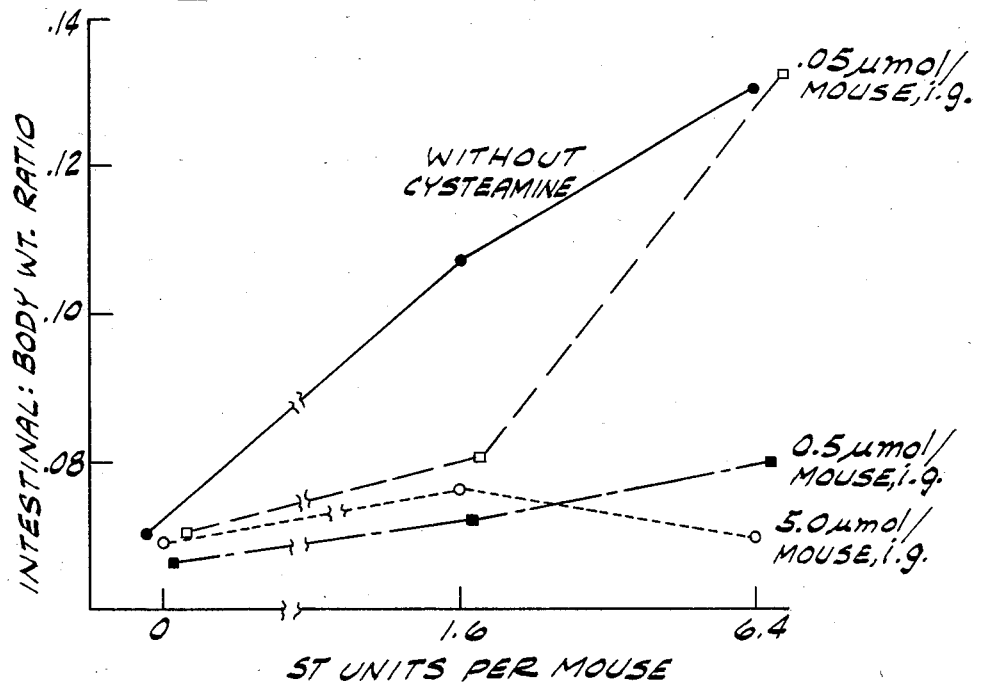
FIG. 2 is a graph depicting the results obtained in studies as to the effect of cysteamine on the inhibition of ST-induced fluid secretion in suckling mice.

Among the disulfides studied, cystamine demonstrated the most inhibition of ST-mediated intestinal fluid secretion. At 0.5 $\mu$mol per mouse, cystamine given s.c. significantly reduced ST-induced intestinal fluid secretion by either 1.6 ST units (from 0.1069±0.003, n=45 to 0.0935±0.003, n=24, P<0.01) or 6.4 ST units (from 0.1298±0.002, n=143 to 0.1154±0.006, n=18, P<0.001) (see FIG. 2). Cystamine at 0.5 $\mu$mol per mouse, i.g., did not significantly affect ST-induced secretion. However, at the one log higher dose, 5 $\mu$mol per mouse, either s.c. or i.g., cystamine significantly reduced ST-induced secretion (FIG. 2). When given at 5 or 0.5 $\mu$mol per mouse either s.c. or i.g., cystamine did not significantly alter basal intestinal fluid levels.

D- and L-cystine

These agents could not be studied at amounts greater then 0.5 $\mu$mol per mouse because of solubility problems. At 0.5 $\mu$mol per mouse, s.c., neither compound reduced intestinal secretion induced by either dose of ST. Using 1.6 ST units per mouse, ST-only resulted in a ratio of 0.113±0.002, n=103; D-cystine, 0.1092±0.011, n=5; L-cystine, 0.1115±0.006, n=6. When administered i.g., both compounds did significantly reduce intestinal fluid secretion induced by 1.6 ST units (from 0.113±0.002, n=103 to 0.1034±0.004, n=23 and 0.0940±0.004, n=15, D- and L-cystine respectively, P 0.05 in each instance) but not by the larger 6.4 ST units dose (from 0.1331±0.003, n=70 to 0.1197±0.004, n=25, and 0.1288±0.003, n=32 D- and L-cystine respectively). Neither agent given s.c. or i.g. significantly altered basal secretion.

Cysteamine

Among the thiol agents, cysteamine showed the greatest inhibitory effect. As little as 0.05 μmol per mouse, i.g., reduced intestinal fluid ratio caused by 1.6 ST units from 0.1069±0.003, n=45 to 0.0804±0.005, n=12, P<0.001. As shown in FIG. 3, cysteamine, i.g., did not alter basal secretion at 0.05, 0.5, and 5.0 μmol per mouse but reduced secretion induced by the larger amount of 6.4 ST units at 0.5 and 5.0 μmol per mouse (P<0.001 in each instance).

Subcutaneously administered cysteamine, 5 μmol/mouse, reduced the 1.6 ST unit ratio from 0.1069±0.003, n=45 to 0.0765±0.003, n=12 and the 6.4 ST unit ratio from 0.1298±0.002, n=143 to 0.0840±0.005, n=12 (P<0.001 in each instance). At a one log lower amount, 0.5 μmol/mouse s.c., the 1.6 ST unit ratio was not significantly changed. Basal fluid level was not affected by either 5 or 0.5 μmol/mouse, s.c.

Acetylcysteine

At 0.5 μmol/mouse, i.g., ST-induced responses by 1.6 ST units (0.1069±0.003, n=45) and by 6.4 ST units (0.1298±0.002, n=143) were significantly reduced to 0.0796±0.005, n=11 and 0.1061±0.005, n=8 respectively (P<0.001 in each instance). Basal fluid level was not affected by either 0.5 or 5 μmol/mouse, given s.c. or i.g. No significant inhibition was evident with a lower amount, 0.05 μmol/mouse. When given s.c., the 1.6 ST unit response was reduced to 0.0804±0.003, n=13 (P<0.01) by a 5 μmol/mouse dose; however, there was no inhibition of the larger 6.4 ST units dose response. Basal fluid level was not altered by 5 μmol/mouse, s.c.

D- and L-cysteine

Both agents when given 0.5 μmol/mouse i.g. reduced ST-induced secretion induced by 1.6 ST units (from 0.1113±0.002, n=103 to 0.0768±0.002, n=8 and to 0.0680±0.001 n=6 (P<0.001 in each instance, D- and L-cysteine respectively) and by 6.4 ST units (from 0.1331±0.003, n=70 to 0.1121±0.005, n=13 and to 0.0877±0.006, n=10 (P<0.01 in each instance, D- and L-cysteine respectively). No effect on basal fluid level was noted at this dose or at 5 μmol/mouse when the agents were given either i.g. or s.c. At 5 μmol/mouse s.c., neither D- or L-cysteine inhibited ST-induced fluid responses caused by either 1.6 ST units or by 6.4 ST units.

Cystathionine

Cystathionine was given i.g. or s.c. at 0.5 μmol/mouse did not inhibit ST-induced fluid secretion nor alter the basal secretory ratio. Higher concentrations of the drug were not studied because of solubility problems.

Lack of inhibition of 8-bromo cyclic GMP-induced intestinal secretion

The effects of the disulfide agents, thiol compounds, and cystathionine on 8-bromo cyclic GMP-induced intestinal fluid secretion in suckling mice was examined (Hughes et al. supra). As reported in Table 2, no agent given either s.c. or i.g. significantly altered 8-bromo cyclic GMP-induced intestinal fluid secretion.

TABLE 2

Lack of inhibition of 8-bromo cyclic GMP*-induced intestinal fluid secretion in suckling mice

| Drug | Dose (μmol/mouse) | Intestinal: Body Wt. Ratio ± SEM i.g. | s.c. |
|---|---|---|---|
| Cystamine | 5.0 | 0.1188 ± 0.003 | 0.1115 ± 0.003 |
| D-cystine | 0.5 | 0.1048 ± 0.004 | 0.1001 ± 0.005 |
| L-cystine | 0.5 | 0.1191 ± 0.004 | 0.1043 ± 0.004 |
| Cysteamine | 5.0 | 0.1106 ± 0.010 | 0.1071 ± 0.005 |
| Acetylcysteine | 5.0 | 0.1028 ± 0.003 | 0.1024 ± 0.003 |
| D-cysteine | 0.5 | 0.1191 ± 0.006 | 0.1155 ± 0.005 |
| L-cysteine | 0.5 | 0.1097 ± 0.004 | 0.1051 ± 0.006 |
| Cystathionine | 0.5 | 0.1043 ± 0.002 | 0.1175 ± 0.004 |

*8-bromo cyclic GMP (in Tris-HCl, 50 mM pH 7.6) = 0.1110 ± 0.002
8-bromo cyclic GMP (in water, pH 7.6) = 0.1099 ± 0.002
Each value is the mean ± SEM of 4 to 59 mice In FIG. 1 each point represents the mean ± standard error of 12 to 143 mice. Symbols ●, no cystamine; ■, cystamine at 0.5 μmol per mouse, s.c.; □, cystamine at 5.0 μmol per mouse, i.g.; ○, cystamine at 5.0 μmol per mouse, s.c. In the dose of 1.6 ST units per mouse, P<0.01 for 0.5 μmol, s.c. and 5.0 μmol, s.c. In the dose of 6.4 units per mouse, P<0.001 for all cystamine administrations.

In FIG. 2, each point represents the mean ± standard error of 6 to 43 mice. Symbols: ●, no cysteamine; □, cysteamine at 0.05 μmol per mouse, i.g.; ■, cysteamine at 0.5 μmol per mouse, i.g.; ○, cysteamine at 5.0 μmol per mouse, i.g. In the dose of 1.6 ST units per mouse, P<0.001 for all cysteamine regimens. In the dose of 6.4 ST units per mouse, P<0.001 for 0.5 μmol and 5.0 μmol cysteamine administrations.

The compound S-2-(3-aminopropylamino) ethyl phosphorothioic acid was also studied in the suckling mouse assay described above.

The results were as follows:

| | Ratio ± SEM | N (number of mice) |
|---|---|---|
| 6.4 units ST | 0.1259 ± 0.005 | 10 |
| 6.4 Units ST, plus .06 mgm/g test compound (i.g.) | 0.1034 ± 0.008 | 5 |
| 6.4 Units ST, plus .6 mgm/g test compound (i.g.) | 0.0685 ± 0.003 | 5 |

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. The method of inhibiting diarrhea induced by *Escherichia coli* heat-stable enterotoxin comprising the administration to mammals afflicted with such diarrhea of a substantially nontoxic material constituting a source of sulfhydryl groups in an effective amount of said material sufficient to inhibit such diarrhea.

2. The method as set forth in claim 1 wherein said substantially nontoxic material constituting a source of sulfhydryl groups is selected from the group consisting of cysteamine, cysteine and acetylcysteine.

3. The method as set forth in claim 2 wherein said substantially nontoxic material constituting a source of sulfhydryl groups is cysteamine.

4. The method as set forth in claim 1 wherein said substantially nontoxic material constituting a source of sulfhydryl groups is a substrate having exposed sulfhydryl groups bound thereto.

5. The method as set forth in claim 4 wherein said substrate is an agarose type gel.

* * * * *